United States Patent [19]

Cano

[11] Patent Number: 4,957,476
[45] Date of Patent: Sep. 18, 1990

[54] AFTERLOADING RADIOACTIVE SPIRAL IMPLANTER

[75] Inventor: Elmer R. Cano, Pittsburgh, Pa.

[73] Assignee: University of Pittsburgh, Pittsburgh, Pa.

[21] Appl. No.: 295,243

[22] Filed: Jan. 9, 1989

[51] Int. Cl.$^5$ ............................................. A61M 36/12
[52] U.S. Cl. ............................................ 600/7; 600/3
[58] Field of Search ........................................ 600/1–7, 600/8, 12; 604/93, 264, 272, 51, 21, 27; 128/897–899

[56] References Cited

U.S. PATENT DOCUMENTS

| | | | |
|---|---|---|---|
| 3,060,924 | 10/1962 | Rush | 600/6 |
| 3,674,006 | 7/1972 | Holmer | 600/7 |
| 4,355,642 | 10/1982 | Alferness | 128/642 |
| 4,584,991 | 4/1986 | Tokita et al. | 600/3 |
| 4,586,490 | 5/1986 | Katz | 600/7 X |

Primary Examiner—Angela D. Sykes
Attorney, Agent, or Firm—Reed, Smith, Shaw & McClay

[57] ABSTRACT

An apparatus for implanting a sealed radioactive source into a patient. The apparatus comprise a hollow member having a sealed end and an opening through which the radioactive source is introduced into the member. The member has a shape that defines an axis such that the member is disposed about the axis. The member is preferably a needle having the shape of a spiral. During implantation, the sealed end of the spiraled needle is inserted into the patient. The needle is then rotated until it is disposed in a desired position in the patient. The radioactive source is then threaded through the opening of the needle such that a predetermined location in the patient is irradiated.

12 Claims, 2 Drawing Sheets

AFTERLOADING RADIOACTIVE SPIRAL IMPLANTER

FIELD OF THE INVENTION

The present invention pertains to brachytherapy. More specifically, the present invention pertains to brachytherapy that is accomplished with a spiraled sealed radioactive source.

BACKGROUND OF THE INVENTION

Brachytherapy, which is the implantation of sealed sources of radioactive material within a tumor, is one of the oldest methods for treating cancer by means of ionized radiation. Interstitial implants are used to treat tumors by inserting afterloading needles into tissue in the vicinity of a tumor and within the tumor itself. See L.W. Brady: Modern Brachytherapy, Masson Ed. Paris, New York, 1987; J.C. Jalabert: Application Methods and Materials of Brachytherapy by Iridium 192, Henri Mondor Hospital.

When straight needles are used, they are usually spaced approximately at 1 to 1.5 cm apart and inserted deep into the tissues as parallel to each other as possible to achieve a uniform dosimetry; nevertheless a great deal of expertise is required for adequate needle placement. In addition, tissue swelling adds significant distortion to the needles, rendering a potentially good implant inappropriate.

The invention described herein provides an accurate radiation dose distribution. The resulting invention provides a shorter operating time with a resulting lessening in risk to the patient during implantation; lower expense; standardization of the dosimetry; elimination of the need for orthogonal films to determine the dosimetry; and less radiation exposure to the implanting physician because of faster loading of the radioactive source into the invention.

SUMMARY OF THE INVENTION

The present invention pertains to an apparatus for implanting a sealed radioactive source into a patient. The apparatus comprises a hollow member having a sealed end, and an opening through which the radioactive source is introduced into the member. The member has a shape that defines an axis such that the member is disposed about the axis. The member is preferably a needle having the shape of a spiral. During implantation, the sealed end of the spiraled needle is inserted into the patient. The needle is then rotated until it is disposed in a desired position in the patient. The radioactive source is then threaded through the opening of the needle such that a predetermined location in the patient is irradiated.

BRIEF DESCRIPTION OF THE DRAWINGS

In the accompanying drawings, the preferred embodiments of the invention and preferred methods of practicing the invention are illustrated in which.

DESCRIPTION OF THE PREFERRED EMBODIMENT

Figure 1:
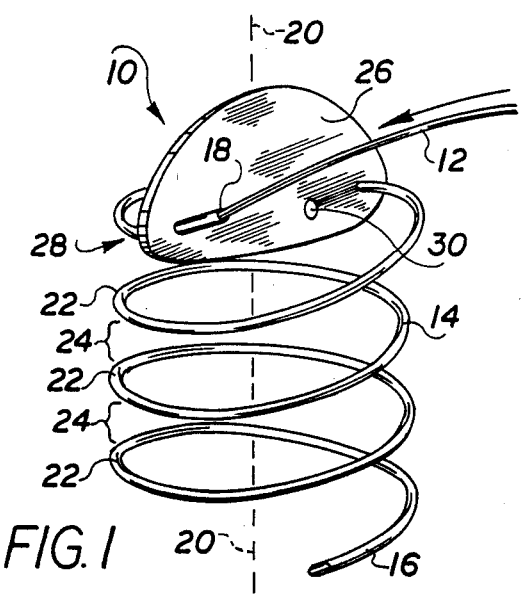
FIG. 1 is a perspective view of an apparatus for implanting a sealed radioactive source into a patient.

Referring now to the drawings, wherein like reference numerals correspond to similar or identical views throughout the several drawings, and more specifically referring to Figure there is shown a perspective view of an apparatus 10 for implanting a sealed radioactive source 12 into a patient. The apparatus 10 is comprised of a hollow member 14 having a sealed end 16, and an opening 18 through which the radioactive source 12 is introduced into the member 14. The member 14 has a shape that defines an axis 20 such that the member 14 is disposed about the axis 20.

Preferably, the member 14 has the shape of a spiral and is made of a material that is both durable and rigid. Preferably, the material the member 14 is made out of is stainless steel.

The member 14 is preferably a needle that has a spiral having a diameter of between 2 cm and 6 cm. The axial length of the spiral is preferably between 3 cm and 7 cm. The spiral forms loops 22 which preferably have a loop spacing 24 between 0.5 cm and 2.5 cm.

The apparatus 10 preferably includes a handle 26 attached to the needle in proximity to the end 28 opposite the sealed end 16. The handle facilitates the insertion of the apparatus 10 into a patient.

In the operation of the preferred embodiment, the area of the patient to be implanted and irradiated is measured and the appropriate apparatus 10 spiral size and length is selected. Under a local or general anesthesia, a small skin incision of approximately 0.5 cm is made in the patient to allow for easy application of the apparatus 10. The end 16 of the spiral is inserted into the skin incision and the apparatus 10 is screwed into place by digital manipulation. The end 28 opposite the sealed end 16 of the apparatus 10 is then secured to the skin with silk threaded through a pin hole 30 in the handle 26.

Once the patient is fully awake, an iridium 192 radioactive source, whose corresponding dosimetry is predetermined by the loop 22 size and axial length of the spiral, is loaded into the patient through opening 18 of the apparatus 10. The radioactive source 12 in the apparatus 10 is maintained in the patient for a period of time predetermined by appropriate dosimetry calculations. Typically, such period of time is as short as 24 hours and as long as 5 days. After that time, the radioactive source 12 is removed, followed by the apparatus 10 being unscrewed from the patient with the aid of the handle 26. The incision is then closed and the patient bandaged.

The apparatus 10 is suitable for the implantation of sealed radioactive sources into a patient at sites which include the tonsillar fossae, floor of the mouth, tongue, prostate, breasts and other soft tissue areas. Accordingly, a single incision is all that is necessary to introduce the apparatus 10 into the patient with the individual loops 22 surrounding a desired area of irradiation. This results in a standardized dosimetry which greatly simplifies and increases the accuracy of this type of radiotherapy.

Figure 2:
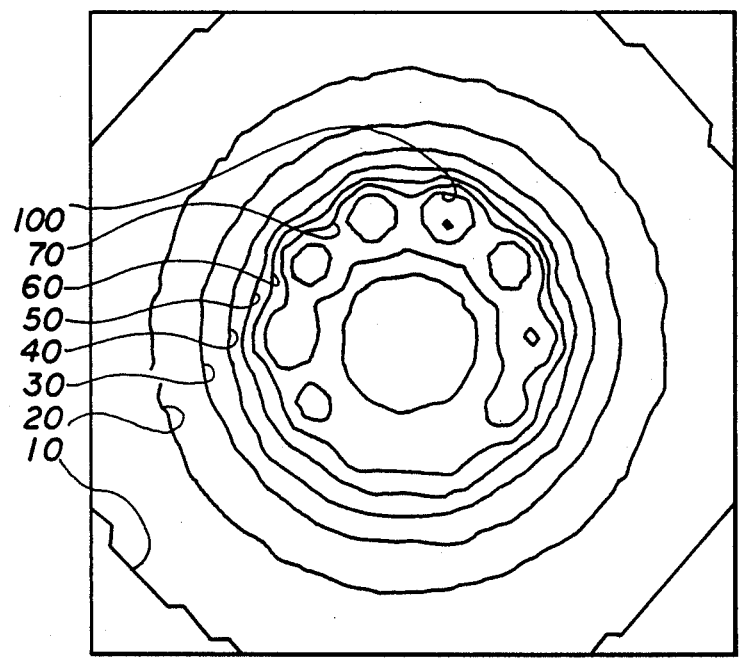
FIG. 2 is an axial cross-sectional view of the resulting isodose distribution for a 3 cm diameter apparatus for implanting a sealed radioactive source into a patient.

An example of a resulting axial cross-sectional view of an isodose distribution for a 3 cm diameter spiral is shown in FIG. 2. The rad/hour lines that constitute the cross-sectional view are identified with a corresponding isodose number. Also, for instance, the 40 rad/hour line has an effective coverage of 4.6 cms when 1.0 mci Ir 192 seeds spaced center to center are used, (seeds are radioactive segments that are lined up in a row and form the radioactive source 12).

Figure 3:
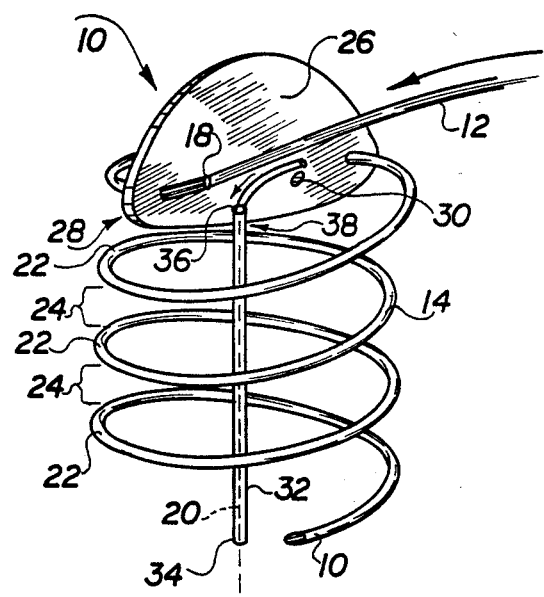
FIG. 3 is a perspective view of an alternative embodiment of an apparatus for implanting a sealed radioactive source into a patient.

In an alternative embodiment, as shown in FIG. 3, there can be included a second hollow member 32 having a sealed end 34 and an opening 36 through which the radioactive source 12 is introduced to the second member 32. The second member 32 is disposed essentially along the axis 20. The handle 26 is attached to the second hollow member 32 in proximity to the end 38 opposite the sealed end 34. Preferably, the second hollow member 32 is a needle that is essentially straight and has a length between 3 cm and 7 cm. The length of the second hollow member 32 is ideally about the same as the axial length of the spiral. The embodiment which includes the second member 32 is preferably used when a spiral having a diameter of 4 cm or more is used. The second member 32 insures that a desired dosimetry level exists at or near the center of the spiral since with the larger diameter spirals, the dosimetry level is lower at or near the spiral axis than the loops 22.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An apparatus for implanting a sealed radioactive source into a patient comprising:
a hollow member substantially spiral in shape having a sealed end, and an opening through which the radioactive source is introduced into the member, said member having a shape that defines an axis such that the member is disposed about the axis.

2. An apparatus as described in claim 1 wherein the member is made of a material that is durable and rigid.

3. An apparatus as described in claim 2 wherein the material is stainless steel.

4. An apparatus as described in claim 3 wherein the member is a needle.

5. An apparatus as described in claim 4 wherein the spiral has a diameter of between 2 cm and 6 cm.

6. An apparatus as described in claim 5 wherein the spiral has an axial length of between 3 cm and 7 cm.

7. An apparatus as described in claim 6 wherein the spiral forms loops having a loop spacing between 0.5 cm and 2.5 cm.

8. An apparatus as described in claim 7 including a handle attached to the needle in proximity to the end opposite the sealed end.

9. An apparatus as described in claim 8 wherein the handle is aligned to the axis of the spiral.

10. An apparatus as described in claim 1 including a handle attached to the hollow member in proximity to the end opposite the sealed end; and a second hollow member having a sealed end, and an opening in the second hollow member through which the radioactive source is introduced to the second member, said second member disposed essentially along the axis, said handle attached to the second hollow member in proximity to the end opposite the sealed end.

11. An apparatus as described in claim 10 wherein the second hollow member is a needle that is essentially straight and has a length of between 3 cm and 7 cm.

12. An apparatus for implanting a sealed radioactive source into a patient comprising:
a hollow needle having a sealed end, and an opening through which the radioactive source is introduced into the needle, said needle having the shape of a spiral, said spiral made out of stainless steel, said spiral having a diameter between 2 cm and 6 cm and an axial length of between 3 cm and 7 cm, said spiral forming loops having a loop spacing between 0.5 cm and 2.5 cm; and
a handle attached to the needle in proximity to the end opposite the sealed end, said handle aligned to the axis of the spiral.

* * * * *